(12) United States Patent
Hans-Moore et al.

(10) Patent No.: US 10,494,604 B2
(45) Date of Patent: Dec. 3, 2019

(54) METHOD AND DEVICE FOR ACTIVATING STEM CELLS

(71) Applicant: DePuy Synthes Products, Inc., Raynham, MA (US)

(72) Inventors: Meredith Hans-Moore, Spring House, PA (US); Doug Buechter, Chester Springs, PA (US); Elliott Gruskin, Malvern, PA (US); Stephen Hornsby, Phoenixville, PA (US); Melissa Brown, Reading, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/091,310

(22) Filed: Apr. 5, 2016

(65) Prior Publication Data

US 2016/0222351 A1    Aug. 4, 2016

Related U.S. Application Data

(62) Division of application No. 12/589,956, filed on Oct. 30, 2009, now abandoned.

(Continued)

(51) Int. Cl.
*A61L 27/38* (2006.01)
*A61K 35/32* (2015.01)
(Continued)

(52) U.S. Cl.
CPC ............ *C12N 5/0654* (2013.01); *A61K 35/32* (2013.01); *A61L 27/12* (2013.01); *A61L 27/18* (2013.01);
(Continued)

(58) Field of Classification Search
None
See application file for complete search history.

(56) References Cited

U.S. PATENT DOCUMENTS 4,522,724 A    6/1985    Ramsden
5,383,931 A    1/1995    Hehli et al.
(Continued)

FOREIGN PATENT DOCUMENTS

CA    2567314    12/2005
JP    2002-509001    3/2002
(Continued)

OTHER PUBLICATIONS

Berdasco et al. "DNA methylation in stem cell renewal and multipotency" Stem Cell Research and Therapy 2011 2:42. Available Oct. 31, 2011 (Year: 2011).*

(Continued)

*Primary Examiner* — Blaine Lankford
*Assistant Examiner* — Lauren K Van Buren
(74) *Attorney, Agent, or Firm* — BakerHostetler

(57) ABSTRACT

Invention embodiments described herein include methods and devices for stimulating mesenchymal stem cells in a stem cell source to differentiate into osteoblasts capable of forming bone. Devices and methods described include exposing a stem cell source, such as bone marrow aspirate, adipose tissue and/or purified allogenic stem cells, to an active agent, in a manner effective to form activated stem cells.

26 Claims, 3 Drawing Sheets

Specification includes a Sequence Listing.

Related U.S. Application Data

(60) Provisional application No. 61/110,096, filed on Oct. 31, 2008, provisional application No. 61/152,335, filed on Feb. 13, 2009.

(51) Int. Cl.
| | |
|---|---|
| *C12M 3/00* | (2006.01) |
| *C12N 5/07* | (2010.01) |
| *C12N 5/077* | (2010.01) |
| *C12N 5/078* | (2010.01) |
| *A61F 2/28* | (2006.01) |
| *A61L 27/12* | (2006.01) |
| *A61L 27/18* | (2006.01) |
| *A61L 27/20* | (2006.01) |
| *A61L 27/46* | (2006.01) |
| *C12N 5/0775* | (2010.01) |

(52) U.S. Cl.
CPC ........... *A61L 27/20* (2013.01); *A61L 27/3834* (2013.01); *A61L 27/3847* (2013.01); *A61L 27/3895* (2013.01); *A61L 27/46* (2013.01); *C12N 5/0663* (2013.01); *C12N 2501/115* (2013.01); *C12N 2501/135* (2013.01); *C12N 2501/15* (2013.01); *C12N 2501/155* (2013.01); *C12N 2506/1346* (2013.01)

(56) References Cited

U.S. PATENT DOCUMENTS

| | | | | |
|---|---|---|---|---|
| 5,874,308 | A * | 2/1999 | Kilburn | C07K 14/475 |
| | | | | 435/383 |
| 6,461,632 | B1 | 10/2002 | Gogolewski | |
| 6,855,329 | B1 | 2/2005 | Shakesheff et al. | |
| 7,044,972 | B2 | 5/2006 | Mathys, Jr. et al. | |
| 7,105,290 | B2 | 9/2006 | Rosenbaum | |
| 7,494,950 | B2 | 2/2009 | Armitage et al. | |
| 2003/0157078 | A1 | 8/2003 | Hall et al. | |
| 2004/0121464 | A1 | 6/2004 | Rathjen et al. | |
| 2005/0227352 | A1 | 10/2005 | Xie | |
| 2005/0249731 | A1 * | 11/2005 | Aslan | A61K 35/28 |
| | | | | 424/144.1 |
| 2006/0008504 | A1 | 1/2006 | Kerr et al. | |
| 2006/0147547 | A1 * | 7/2006 | Yayon | A61K 31/195 |
| | | | | 424/602 |
| 2006/0153818 | A1 * | 7/2006 | Dhanaraj | C12N 5/0605 |
| | | | | 424/93.7 |
| 2006/0154366 | A1 | 7/2006 | Brown et al. | |
| 2006/0182724 | A1 * | 8/2006 | Riordan | A61K 8/982 |
| | | | | 424/93.7 |
| 2007/0065420 | A1 | 3/2007 | Johnson | |
| 2007/0135843 | A1 | 6/2007 | Burkhart | |
| 2007/0191276 | A1 | 8/2007 | Lee et al. | |
| 2008/0261305 | A1 * | 10/2008 | Hantash | C12N 5/0654 |
| | | | | 435/378 |

FOREIGN PATENT DOCUMENTS

| | | | | |
|---|---|---|---|---|
| JP | 2011-509656 | | 3/2011 | |
| WO | WO 2007/093431 | | 8/2007 | |
| WO | WO-2007093431 | A1 * | 8/2007 | ........... C12N 5/0654 |
| WO | WO 2007/108689 | | 9/2007 | |
| WO | WO200708689 | * | 9/2007 | |
| WO | WO-2007108689 | A2 * | 9/2007 | ........... C12N 5/0654 |
| WO | WO 2010/051032 | | 5/2010 | |

OTHER PUBLICATIONS

Akita et al., Cranial bone defect healing is accelerated by mesenchymal stem cells induced by coadministration of bone morphogenetic protein-2 and basic fibroblast growth factor. Wound Repair Regen, Mar.-Apr. 2004, 12(2), 252-259.

Doucet et al., Platelet lysates promote mesenchymal stem cell expansion: a safety substitute for animal serum in cell-based therapy applications. J Cell Physiol., Nov. 2005, 205(2), 228-236.

International Application Serial No. PCT/US2009/005910, International Search Report dated Jan. 11, 2010, 5 pgs.

International Application Serial No. PCT/US2009/005910, Written Opinion dated Jan. 11, 2010, 9 pgs.

Antoniades, H. N., et al., Human Platelet-Derived Growth Factor (PDGF): Amino-Terminal Amino Acid Sequence, Science 220(4600), May 1983, 963-965.

Behringer, R., R., et al., Abnormal sexual development in transgenic mice chronically expressing Müllerian inhibiting substance, Nature (6271), May 1990, 167-170.

Beresford, J. N., et al., Osteogenic Stem Cells and the Stromal System of Bone and Marrow, Clin. Orthop. Relat. Res., 240, Mar. 1989, 270-280.

Betsholtz, C., et al., cDNA sequence and chromosomal localization of human platelet-derived growth factor A-chain and its expression in tumour cell lines, Nature, 320(6064), Apr. 1986, 695-699.

Bollo, A., et al., Different Forms of Bone Grafts, The Journal of Foot and Ankle Surgery, 35(5), Sep.-Oct. 1996, 400-405.

Collins, T., et al., Cultured human endothelial cells express platelet-derived growth factor B chain: cDNA cloning and structural analysis, Nature 316(6030), Aug. 1985, 748-750.

Dalla-Favera, R., et al., Chromosomal Localization of the Human Homolog (c-sis) of the Simian Sarcoma Virus onc Gene, Science, 218(4573) Nov. 1982, 686-688.

Doolittle, R. F., et al., Simian Sarcoma Virus onc Gene, v-sis is Derived from the Gene (or Genes) Encoding of Platelet-Derived Growth Factor, Science, 221(4607), Jul. 1983, 275-277.

Hogan, B.L. M., Bone morphogenetic proteins: multifunctional regulators of vertebrate development, Genes & Development, 10(13), Jul. 1996, 1580-1594.

Jaiswal, N., et al, Osteogenic Differentiation of Purified, Culture-Expanded Human Mesenchymal Stem Cells In Vitro, Journal of Cellular Biochemistry, 64(2), Feb. 1997, 295-312.

Mason, A. J., et al., Structure of Two Human Ovarian Inhibins, Biochemical and Biophysical Research Communications, 135(3), Mar. 1986, 957-964.

Massagué, J., TGF-β Signal Transduction, Annu. Rev. Biochem, 67, Jul. 1998, 753-791.

Matsuda, C., et al., Differentiation of Human Bone Marrow Mesenchymal Stem Cells to Chondrocytes for Construction of Three-dimensional Cartilage Tissue, Chytotechnology, 47(1-3), Jan. 2005, 11-17.

Mehlhorn, A. T., et al., Mesenchymal Stem Cells Maintain TGF-β-Mediated Chondrogenic Phenotype in Alginate Bead Culture, Tissue Engineering 12(6), Jun. 2006, 1393-1403.

Ornitz, D. M., FGFs, heparan sulfate and FGFRs: complex interactions essential for development, BioEssays, 22, Feb. 2000, 108-112.

Ornitz, D. M, et al., Fibroblast growth factors, Genome Biology, 2(3), Mar. 2001, 3005.1-3005.12.

Padgett, R. W. et al., A transcript from a *Drosophila* pattern gene predicts a protein homologous to the transforming growth factor-β family, Nature, 325(6099), Jan. 1987, 81-84.

Pelttari, K., et al., The use of mesenchymal stem cells for chongrogenesis, Injury 39(1), Apr. 2008, 58-65.

Rao, C.D., et al., Structure and sequence of the human c-sis/platelet-derived growth factor 2 (SIS/PDGF2) transcriptional unit, Proc. Natl. Acad. Sci. USA, 83, Apr. 1986, 2392-2396.

Reddi, A. H., Bone Morphogenetic Proteins: an Unconventional Approach to Isolatin of First Mammalian Morphogens, Cytokine & Growth Factor Reviews, 8(1), Mar. 1997, 11-20.

Sampath, T.K. et al., Bovine Osteogenic Protein Is Composed of Dimers of OP-1 and BMP-2A, Two Members of the Transforming Growth Factor-β Superfamily, The Journal of Biological Chemistry, 265(22), Aug. 1990, 13198-13205.

Singhatanadgit, W. et al., Up-Regulation of Bone Morphogenetic Protein Receptor IB by Growth Factors Enchances BMP-2-Induced Human Bone Cell Functions, Journal of Cellular Physiology, 209(3), Dec. 2006, 912-922.

(56) References Cited

OTHER PUBLICATIONS

Weeks, D.L. et al., A Maternal mRNA Localized to the Vegetal Hemisphere in Xenopus Eggs Codes for a Growth Factor Related to TGF-β, Cell, 51, Dec. 1987, 861-867.

Xu, D., et al., Potential involvement of BMP receptor type IB activation in a synergistic effect of chondrogenic promotion between rhTGFβ3 and rhGDF5 or rhBMP7 in human mesenchymal stem cells, Growth Factors, 24(4), Dec. 2006, 268-278.

Yamashita, H., et al., Bone Morphogenetic Protein Receptors, Bone 19(6), Dec. 1996, 569-574.

Yeh, L.C.C. et al., Osteogenic Protein-1 Differentially Regulates the mRNA Expression of Bone Morphogenetic Proteins and Their Receptors in Primary Cultures of Osteoblasts, Journal of Cellular Physiology, 185(1), Oct. 2000, 87-97.

Arthrex Reference Document, "Arthrex is Reaching New Heights in Rotator Cuff Repair" 2007, 8 pages.

Thomsen, G. et al., Activins are expressed early in Xenopus embryogenesis and can induce axial mesoderm and anterior structures, Cell 63.3, Nov. 1990: 485-493.

Massague, J., The TGF-β family of growth and differentiation factors, Cell, 49(4), May 1987, 437-438.

Ling, Pituitary FSH is released by a heterodimer of the beta-subunits from the two forms of inhibin, Nature, 321(6072): 779-82, Jun. 1986.

Cheifetz, et al., The transforming growth factor-β system, a complex pattern of cross-reactive ligands and receptors, Cell 48,3, Feb. 1987, 409-415.

Robbins, et al., Structural and immunological similarities between simian sarcoma virus gene product(s) and human-platelet-derived growth factor, Nature 305, Oct. 1983, 605-608.

Yeh, et al., Osteogenic protein-1 and interleukin-6 with its soluble receptor synergistically stimulate rat osteoblastic cell differentiation, Journal of cellular physiology 190.3, Mar. 2002, 322-331.

Yeh, et al., Differential effects of osteogenic protein-1 (BMP-7) on gene expression of BMP and GDF family members during differentiation of the mouse MC615 chondrocyte cells, Journal of cellular physiology 191.3, Jun. 2002, 298-309.

Scaglione et al., Engineering of Osteoinductive Grafts by Isolation and Expansion of Ovine Bone Marrow Stromal Cells Directly on 3D Ceramic Scaffolds, Biotechnology and Bioengineering, V93, No. 1, 181-187, Jan. 2005.

Li-Yan et al., Advances of Studies on Mesenchymal Stem Cells, Chinese Journal of Biotechnology, Mar. 2003, vol. 19, No. 2, 136-140 (with Abstract).

Akihito Minamide et al: "The Effects of Bone Morphogenetic Protein and Basic Fibroblast Growth Factor on Cultured Mesenchymal Stem Cells for Spine Fusion", Spine, vol. 32, Jan. 1, 2007, pp. 1067-1071.

Barbara Margosio et al: "Fibroblast Growth Factor-2 Binding to The Thrombospondin-1 Type III Repeats, A Novel Antiangiogenic Domain NIH Public Access Introduction", Int J Biochem Cell Biol, Jan. 1, 2008 (Jan. 1, 2008), pp. 700-709, XP055420888.

Li Fuzeng et al., Modern Traumatology, Jilin Science and Technology Press, p. 236, published in Jun. 2007.

Jiao Kui et al., Enzyme-linked Immunosorbent Assay Technology and Application, Chemical Industry Press, pp. 248-255, published in Aug. 2004.

English Translation of CN Office Action dated Jul. 18, 2018 for CN Application No. 201410589910.

Yamada et al., Autogenous injectable bone for regeneration with mesenchymal stem cells and platelet-rich plasma: tissue-engineered bone regeneration. Tissue engineering. May 1, 2004;10(5-6):955-964.

Yoon et al., Bmp1a and Bmpr1b have overlapping functions and are essential for chondrogenesis in vivo, PNAS, 102(14), 2005, 5062-5067.

Solchaga et al, FGF-2 Enhances the Mitotic and Chondrogenic Potentials of Human Adult Bone Marrow-Derived Mesenchymal Stem Cells, J. Cell Physiol., 2005, 203(2), 398-409.

Handorf, et al., Fibroblast Growth Factor-2 Primes Human Mesenchymal Stem Cells for Enhanced Chondrogenesis, PLOS ONE, 6(7), 1-11, e22887; Jul. 2011.

Bruder et al, Bone Regeneration by Implantation of Purified, Culture-Expanded Human Mesenchymal Stem Cells, Journal of Orthopaedic Research,1998,16:155-162.

* cited by examiner

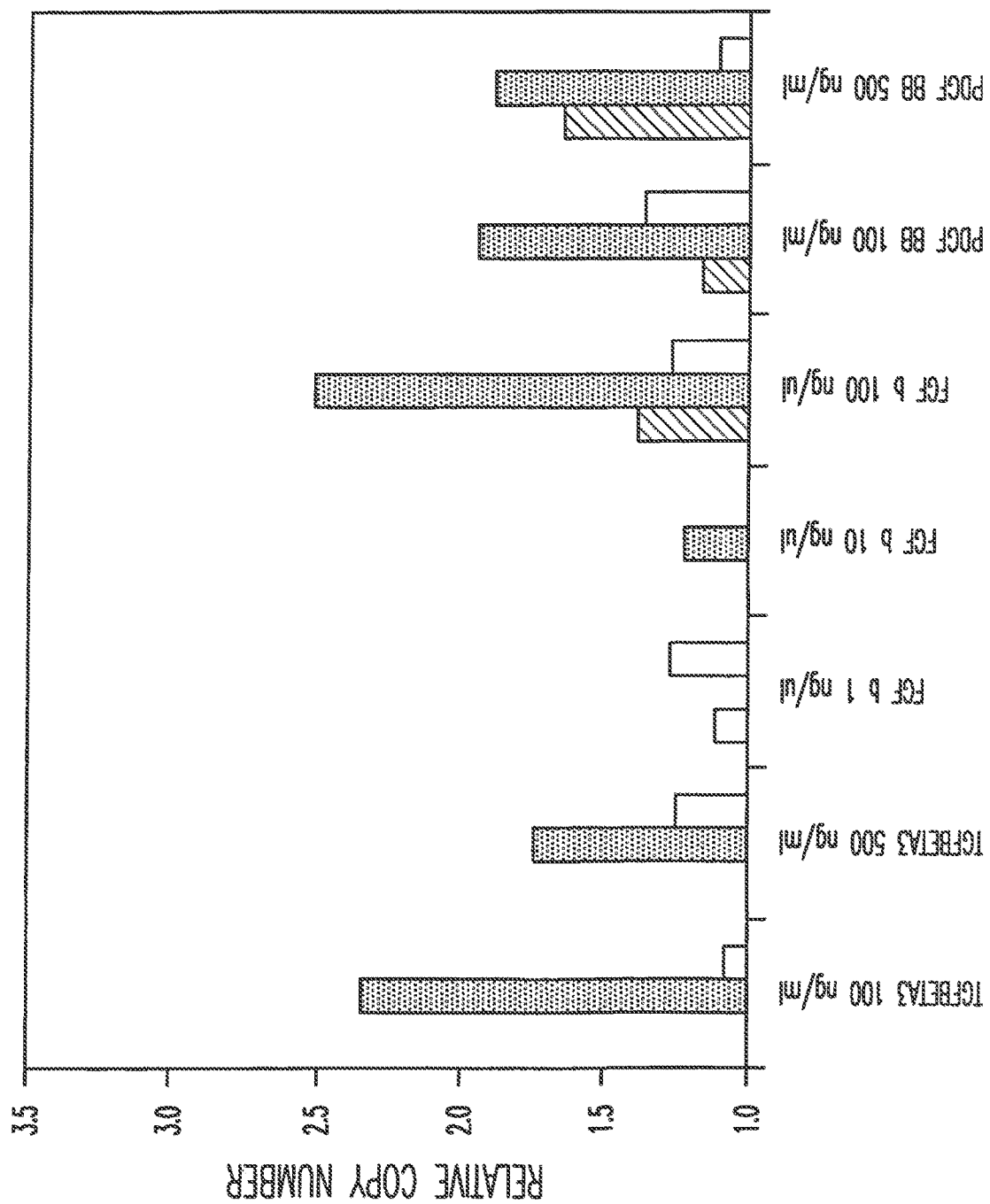

METHOD AND DEVICE FOR ACTIVATING STEM CELLS

RELATED APPLICATIONS

This application is a divisional application of U.S. patent application Ser. No. 12/589,956, filed Oct. 30, 2009 (pending), which claims the benefit of the filing date of U.S. Provisional Patent Application Ser. No. 61/110,096, filed Oct. 31, 2008, and entitled, "DEVICE FOR ACTIVATING BONE MARROW ASPIRATE USING EX VIVO STIMULATION BY GROWTH FACTORS FOR IMPROVED BONE FORMATION", and of U.S. Provisional Patent Application Ser. No. 61/152,335, filed Feb. 13, 2009, and entitled, "METHOD AND DEVICE FOR FORMING A BONE MARROW ASPIRATE PRODUCT", the contents of each of which are incorporated herein by reference in their entirety.

FIELD

Inventive subject matter described herein relates to devices and methods for activating stem cells, including activating stem cells in bone marrow aspirate using ex vivo stimulation. The inventive subject matter also relates to implants containing such activated stem cells.

BACKGROUND OF THE INVENTION

In order to provide for maximum bone formation, it is desirable to transplant cells that already exhibit an osteoblastic phenotype, because such cells likely to exhibit bone-forming activity. However, in vitro differentiation of bone marrow stem cells into osteoblasts involves culturing in osteogenic medium (Jaiswal et al. 1997. J Cell Biochem 64: 295-312) and may lead to decreased proliferation of such cells in vitro. Moreover, the use of osteogenic medium involves addition of components to the cells (e.g., growth factors) that can have unintended side effects if those components are administered to a patient along with the cells.

Hence, there exists a need in the art for a simple and reliable method to produce osteoprogenitors, osteoblasts or osteoblastic phenotypic cells in vitro from stem cells, for example, human bone marrow stem cells, where the desirable cells are readily separated from the factors used for generating the osteoprogenitors, osteoblasts or osteoblastic phenotypic cells.

SUMMARY OF THE INVENTION

One aspect of the invention is a method for preparing a implant composition for promoting bone growth in a mammal, comprising (a) contacting stem cells with one or more active agents for 24 hours or less to prepare an activated stem cells, (b) separating the active agents from the activated stem cells to form an activated stem cell population that is substantially free of active agents, and (c) mixing the activated stem cell population that is substantially free of active agents with a bone graft substitute to thereby prepare an implant composition for promoting bone growth in a mammal, wherein at least one active agent promotes differentiation of stem cells into osteogenic cells or osteogenic precursor cells. The osteogenic cells and/or osteogenic progenitor cells can be osteoprogenitors, osteoblasts or osteoblastic phenotypic cells. In some embodiments, the stem cells are contacted with one or more active agents for 5 minutes to 1 hour. In other embodiments, the stem cells are contacted with one or more active agents for 5 minutes to 0.5 hours. The stem cells can, for example, be obtained or isolated from bone marrow, adipose tissue, muscle tissue, umbilical cord blood, embryonic yolk sac, placenta, umbilical cord, periosteum, fetal skin, adolescent skin, or blood. The stem cells can be embryonic, post-natal or adult stem cells. In some embodiments, the stem cells are autologous, allogeneic or xenogenic. The stem cells can include mesenchymal stem cells. Such mesenchymal stem cells can include autologous bone marrow aspirate. The bone marrow aspirate can be drawn intraoperatively. After obtaining the stem cells they can be concentrated so that unnecessary liquid is removed. Alternatively, the stem cells can be isolated from the tissue or liquid from which they were initially obtained.

The active agents can, for example, regulate cellular growth and/or differentiation, and may be selected from the group consisting of small molecules, peptides, growth factors, cytokines, ligands, hormones and combinations thereof. Examples of active agents include active agents such as transforming growth factor beta (TGF-β), fibroblast growth factor (FGF), platelet-derived growth factor (PDGF), bone morphogenic protein (BMP), insulin growth factor (IGF), interleukin-I (IL-I), interleukin-11 (IL-11), simvastatsin, dexamethasone, oxysterol, sonic hedgehog, interferon, tumor necrosis factor, nerve growth factor (NGF), fibronectin, RGD peptide, integrin, epidermal growth factor (EGF), hepatocyte growth factor (HGF), keratinocyte growth factor, osteogenic protein, and combinations thereof. In some embodiments, the active agents are selected from the group consisting of BMP-2, TGF-beta3, PDGF-AB, PDGF-BB, FGF-2, TGF-beta1, BMP-4, BMP-7, BMP-6, FGF-8, IL-11, simvastatsin, dexamethasone, oxysterols, sonic hedgehog, and combinations thereof. In other embodiments, the active agents include TGF-8 and FGFb, and can further include PDGF. The active agents can be from an autologous source. The active agents can be used in the method while in solution. When the active agents are used in the methods while in solution, the activated stem cells are separated pursuant to step (b) from the active agents by a procedure that includes filtration, gel filtration, tangential flow filtration, immunoprecipitation, immuno-absorption, column chromatography or a combination thereof. In other embodiments, the active agents are attached to a solid support. For example, at least some of the active agents can be directly or indirectly attached to a solid support by covalent attachment, adsorption, non-covalent interaction and/or combinations thereof. In some embodiments, at least some of the active agents are attached to the solid support via a peptide, an antibody, a chemical cross linker, an alkylene chain or a combination thereof.

The bone graft substitute can include materials such as calcium salts. Such calcium salts can, for example, include monocalcium phosphate monohydrate, α-tricalcium phosphate, β-tricalcium phosphate, calcium carbonate, or a combination thereof. The bone graft substitute can further include demineralized bone, a sodium phosphate salt, a polymer or a combination thereof. Such a polymer can be collagen, gelatin, hyaluronic acid, a hyaluronate salt, hydroxypropylcellulose (HPC), carboxymethylcellulose (CMC), hydroxypropyl methylcellulose (HPMC), hydroxyethylcellulose (HEC), xantham gum, guar gum, alginate or a combination thereof. In some embodiments, the methods increase expression of alkaline phosphatase and/or a bone morphogenetic protein (BMP) receptor subunit in the stem cells. Such methods can further include implanting the implant composition into a patient.

Another aspect of the invention is an implant composition prepared by the methods described herein.

Another aspect of the invention is a method for treating a bone injury, disorder or condition in a subject comprising administering an implant composition described herein to a site of the bone injury, disorder or condition in the subject. Such a bone injury, disorder or condition can be a broken bone, a bone defect, a bone transplant, a bone graft, bone cancer, a joint replacement, a joint repair, a bone fusion, a bone facet repair, bone degeneration, a dental implant, a dental repair, arthritis, bone reconstruction, or a combination thereof.

Another aspect of the invention is a device for activating a stem cell that includes a solid support and at least one active agent that promotes differentiation of stem cells into osteogenic cells or osteogenic precursor cells, wherein the device is adapted: (i) for incubating the stem cell with the at least one active agent, and (ii) for separating the at least one active agent from the stem cell after the incubating step (i). For example, the at least one active agent is selected from the group consisting of transforming growth factor beta (TGF-β), fibroblast growth factor (FGF), platelet-derived growth factor (PDGF), bone morphogenic protein (BMP), insulin growth factor (IGF), interleukin-I (IL-I), interleukin-11 (IL-11), simvastatsin, dexamethasone, oxysterol, sonic hedgehog, interferon, tumor necrosis factor, nerve growth factor (NGF), fibronectin, RGD peptide, integrin, epidermal growth factor (EGF), hepatocyte growth factor (HGF), keratinocyte growth factor, osteogenic protein, and combinations thereof.

In some embodiments, the at least one active agent is selected from the group consisting of BMP-2, TGF-beta3, PDGF-AB, PDGF-BB, FGF-2, TGF-beta1, BMP-4, BMP-7, BMP-6, FGF-8, IL-11, simvastatsin, dexamethasone, oxysterols, sonic hedgehog, and combinations thereof. In other embodiments, the at least one active agent includes TGF-β and FGFb, and can further include PDGF. The at least one active agent can, for example, be from an autologous source. The active agent(s) can be in solution within the solid support or attached to the solid support. The active agent can, for example, be attached to the solid support via an antibody or peptide that binds at least one active agent.

The solid support can include a column matrix material, a filter, an culture plate, tube or dish, a microtiter plate, a bead, a disk, or a combination thereof. The solid support can be a container. The solid support can include plastic, cellulose, cellulose derivatives, magnetic particles, nitrocellulose, glass, fiberglass, latex, or a combination thereof. The solid support can also include an affinity matrix to remove the at least one active agent. When a filter is present in the solid support, the filter can retain cell and bone graft substitute materials but allow passage of the at least one active agent. Alternatively, the filter can retain the at least one active agent but allow passage of the stem cells. In some embodiments, the solid support does not bind or adversely interact with stem cells. In other embodiments, the solid support can bind the stem cells without adversely interacting with the stem cells.

The device can further include a timer for controlling the time for incubating the stem cells with the at least one active agent. For example, the timer can trigger separation of the at least one active agent from the stem cell after the incubating step (i). In some embodiments, the device with the timer controls the time for incubating the stem cells with the at least one active agent to 24 hours or less. In other embodiments, the device with the timer controls the time for incubating the stem cells with the at least one active agent to 5 minutes to 1 hour.

Another aspect of the invention is a device for bone formation comprising a first component for handling a stem cell source; and a second component for exposing the stem cell source to an active agent in a manner effective to stimulate mesenchymal stem cells in the stem cell source to differentiate into osteoblasts, wherein the osteoblasts can be incorporated into an implant composition useful for repair and/or generation of bone. The stem cell source can be bone marrow aspirate, including autologous bone marrow aspirate, adipose tissue and/or purified allogenic stem cells.

The active agent can include, but is not limited to BMP-2, TGF-beta3, PDGF-AB, PDGF-BB, FGF-2, TGF-beta1, BMP-4, BMP-7, BMP-6, FGF-8, IL-11, simvastatsin, dexamethasone, oxysterols and/or sonic hedgehog. The active agent may be directly attached to a solid support of the device or tethered to the solid support, for example, through a linker. In one embodiment, in the tether is selected from an alkylene chain, a peptide, an antibody, a chemical cross linker, and combinations thereof.

In one embodiment, the active agent is in solution, and the second component can further comprise a filter component or an affinity matrix (e.g., with a peptide or antibody) for removing the active agent from the mesenchymal stem cells.

One embodiment includes a device for activating bone marrow aspirate. The device comprises a component for mixing a bone graft substitute and a bone marrow aspirate drawn from a patient to form a mixture. The device also includes a component for transiently exposing the mixture to a fixed or tethered active agent in a manner effective for triggering mesenchymal stem cells to enhance an osteoblast phenotype.

Another embodiment includes a device for activating bone marrow aspirate which includes a component for handling bone marrow aspirate drawn from a patient. The device also includes a component for exposing the bone marrow aspirate to an active agent in a manner effective for triggering mesenchymal stem cells to enhance an osteoblast phenotype.

Another device for activating bone marrow aspirate is described, including a component for mixing a bone graft substitute and a bone marrow aspirate drawn from a patient to form a mixture. The device further includes a component for exposing the mixture to a fixed or tethered active agent in a manner effective for triggering mesenchymal stem cells to enhance an osteoblast phenotype. Following exposure, BMA is separated from tethered or fixed active agent and can be mixed with a bone graft substitute.

In one embodiment, a method comprising exposing a stem cell source (e.g., bone marrow aspirate, including autologous bone marrow aspirate) to an active agent, wherein mesenchymal stem cells in the stem cell source are stimulated to differentiate into osteoblasts. In one embodiment, the bone marrow aspirate is drawn intraoperatively and/or used in a form as drawn from the patient. Alternatively, the bone marrow aspirate can further be concentrated after it is drawn from the patient. The method can also include mixing stimulated or activated stem cells (e.g., mesenchymal stem cells) with a synthetic bone graft substitute to form a mixture, wherein the exposing comprises transiently exposing the mixture to a fixed or tethered active agent in a manner effective for triggering mesenchymal stem cells to enhance an osteoblast phenotype.

In one embodiment, the active agent is bonded to a substrate to form a bonded substrate. In this embodiment, the stem cell source is incubated with the bonded active agent for a period of time, such as between 5 minutes and 24 hours, or between 5 minutes and 1 hour, or between 15 minutes and 1 hour. In one embodiment, the incubating causes upregulation in a bone morphogenetic protein (BMP) receptor subunit in the bone.

In one embodiment, the exposing of a stem cell source to an active agent occurs in a stem cell solution, and the method can further comprise removing the active agent from the stem cell solution, such as with formation of an affinity matrix and/or filtration.

In another embodiment, a method is provided for forming progenitor cells capable of stimulating bone formation. Method operations include mixing bone marrow aspirate (BMA) with an active agent, and using the active agent to trigger mesenchymal stem cells (MSCs) to enhance an osteoblast phenotype. Such a method can trigger mesenchymal stem cells to enhance or develop an osteoblast phenotype. The method can also include mixing a bone graft substitute and a bone marrow aspirate drawn from a patient to form a mixture; and transiently exposing the mixture to a fixed or tethered active agent in a manner effective for triggering mesenchymal stem cells to enhance or develop the osteoblast phenotype.

In some embodiments, the method further includes implanting stimulated mesynchemal stem cells in a patient, which may include implanting the active agent together with the stem cell source.

DESCRIPTION OF THE DRAWINGS

FIG. 3 graphically illustrates relative mRNA copy number of three BMP receptor units (namely -1A, -1B and II) after primary MSCs were exposed to PDGF BB, FGF b and TGF beta3 for one (1) hour using concentrations of 1 ng/ml, 10 ng/ml and 100 ng/ml. Cells were harvested and subjected to a quantitative PCR for all three BMP receptor units (namely -1A, -1B and II) as described in Example 1.

DETAILED DESCRIPTION

Figure 1:
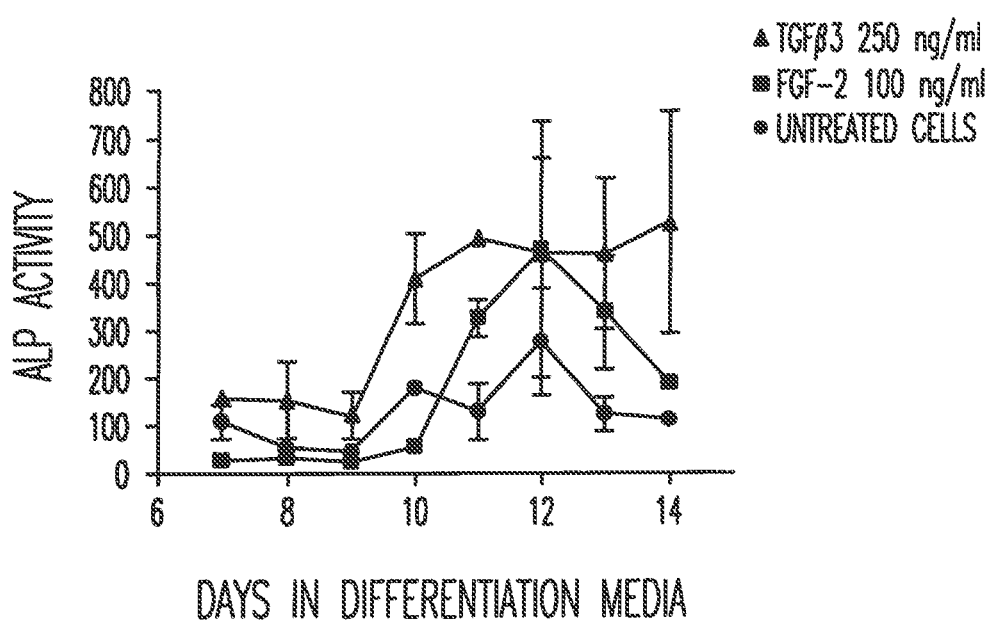
FIG. 1 graphically illustrates the levels of alkaline phosphatase expressed by primary human MSC's in embodiments of the present invention. The cells were cultured in differentiation media following a 1 hour treatment with fibroblast growth factor (hereinafter "FGF-2") (100 ng/ml) or TGF beta3 (250 ng/ml). The levels of alkaline phosphatase expressed by the cells were then measured using the assay described in Example 1.

In the current state of the art, a bone marrow aspirate (hereinafter "BMA") is drawn from a patient intraoperatively, mixed with a bone graft substitute and re-implanted in the surgical site to promote bone healing. However, while bone marrow aspirate may contain some connective tissue progenitor cells that may produce osteoblasts, there is a wide patient to patient variation in the number and type of osteogenic cells that can actually promote bone formation.

Described herein are methods, devices and implants that improve the performance of stem cells (e.g., BMA), either by increasing in cell number or by an increasing in the osteogenic potential of the progenitor cells in the BMA or stem cell mixture. Embodiments described herein include methods and devices to briefly, intraoperatively expose stem cells ex vivo, to one or more exogenous active agents, to thereby generate progenitor cells that are capable of stimulating bone growth, where the active agent(s) are then removed from the stem cells (i.e., progenitor cells activated by the active agents). The active agent(s) can be, for example, a small molecule, a peptide, a growth factor, cytokine, ligand or other factor. The active agent(s) can be captured from an autologous source, be obtained from a commercial source or be manufactured (e.g., by recombinant procedures).

In some embodiments, the active agents are capable of increasing the expression of bone morphogenetic protein, hereinafter BMP, receptor subunit(s) in the progenitor cells of the stem cell mixture. This treatment by the active agents helps, for example, to potentiate the ability of the progenitor cells to respond to endogenous BMPs at the site of bone injury or bone surgery. Such treatment with active agents can also drive the stem cells to differentiate down an osteoblast pathway. While stem cells have been activated by treatment with cytokines for extended periods of time (e.g., several days), as described herein, exposure of stem cells to active agents for such extended periods of time is not necessary: stem cells can be activated and exhibit osteogenic potential after exposure to active agents for only about 15 minutes to about 3 hours.

Moreover, some studies indicate that the existence of an accessory cell population that might be necessary for the outgrowth of bone precursor cells in vitro. Thus, highly purified bone precursor cells may fail to multiply, even in the presence of a cocktail of osteogenic cytokines. Thus, extended culturing of stem cells may not be advantageous. The methods and devices described herein do not involve extended periods of culturing cells and are faster and thereby avoid the potential for contamination and the expenses associated with extended cell culture.

As described herein potentiation, activation and/or differentiation of stem cells to have osteogenic potential can be accomplished by tethering the active agent(s) onto or within a device so that cells contained within stem cell mixture can be activated, and easily separated from the active agent(s), for example, by removing the cells from the device. Separating the active agents from the cells before implantation of the cells reduces the potential for unintended side effects from the active agents themselves (e.g., stimulating undesired responses or inducing harmful immune responses).

Stem Cell Sources

The methods, devices and implants described herein can employ stem cells from any convenient source. However, stem cells that have osteogenic potential or that can be treated (e.g., differentiated) to generate cells with osteogenic potential are preferred.

Sources of stem cells that can be used in the methods, devices and implants described herein include bone marrow, adipose tissue, muscle tissue, ex vivo cultured autologous mesenchymal stem cells, allogeneic off-the-shelf mesenchymal stem cells, umbilical cord blood, embryonic yolk sac, placenta, umbilical cord, periosteum, fetal and adolescent skin, and blood. In some embodiments, the stem cells are mesenchymal stem cells or a mixture of cells that include mesenchymal stem cells (e.g., bone marrow aspirate). The stem cells can be autologous, allogeneic or from xenogeneic sources. The stem cells can be embryonic or from post-natal or adult sources.

Bone marrow aspirate is one source of stem cells useful in the methods, devices and implants described herein. While such bone marrow aspirate can be autologous, allogeneic or from xenogeneic sources, in some embodiments the bone marrow aspirate is autologous.

Bone marrow aspirate contains a complex mixture of hematopoietic stem cells, red and white blood cells and their precursors, mesenchymal stem and progenitor cells, stromal cells and their precursors, and a group of cells including fibroblasts, reticulocytes, adipocytes, and endothelial cells which form a connective tissue network called "stroma." Cells from the stroma morphologically regulate the differentiation of hematopoietic cells through direct interaction via cell surface proteins and the secretion of growth factors and are involved in the foundation and support of the bone structure. Studies indicate that bone marrow contains "prestromal" cells which have the capacity to differentiate into cartilage, bone, and other connective tissue cells. Beresford "Osteogenic Stem Cells and the Stromal System of Bone and Marrow", Clin. Orthop., 240:270, 1989. Recent evidence indicates that these cells, called pluripotent stromal stem cells or mesenchymal stem cells, have the ability to generate into several different types of cell lines (i.e., osteocytes, chondrocytes, adipocytes, etc.) upon activation. However, mesenchymal stem cells are often present in bone marrow aspirates in very minute amounts with a wide variety of other cells (i.e., erythrocytes, platelets, neutrophils, lymphocytes, monocytes, eosinophils, basophils, adipocytes, etc.). In addition, their ability to differentiate into an assortment of connective tissues depends not only on the presence of bioactive factors in the aspirate, which can vary, but is also, to some extent, dependent upon the age of the donor. The methods and devices described herein address these problems by improving the numbers of cells in the stem cell sample and the potential for the stem cells to differentiate into osteoblasts.

In some embodiments, the stem cells include mesenchymal stem cells. Mesenchymal stem cells can be identified by procedures available to those of skill in the art. For example, mesenchymal stem cells can be identified via colony forming unit assays (CFU-f) or via flow cytometry using markers that are typically expressed by mesenchymal stem cells. Mesenchymal stem cells generally express such markers as $CD271^+$, $CD105^+$, $CD73^+$, but exhibit a $CD34^-$ and $CD45^-$ phenotype.

When bone marrow cells are employed, these cells may be obtained from iliac crest, femora, tibiae, spine, rib or other medullary spaces. In some embodiments, the stem cells are from an autologous fluid (e.g., bone marrow aspirate). Borne marrow aspirate is a good source of mesenchymal stem cells.

The stem cells can, in some embodiments, be subjected to a separation process such as centrifugation, size filtration, immunomagetic selection, etc., in order to either screen out "irrelevant" cells, and improve the efficiency of the activation step, or to preselect for mesenchymal stem cells to facitilate bone formation in implant materials. While it may not be necessary to separate the cell types and/or purify the mesenchymal stem cells, it some embodiments it may be desirable.

When separation of cell types is desired, a biological sample, for example, comprising bone marrow can be centrifuged to separate the components of the sample into various fractions based on density, including a fraction rich in connective tissue growth promoting components such as mesenchymal stem cells. The fraction rich in connective tissue growth promoting components can then be isolated. In addition, the biological sample that is centrifuged can be free from cell culture medium materials. In some embodiments, the biological sample that is centrifuged can consist essentially of tissue material (e.g. bone marrow material optionally in combination with blood or other tissue material) from a patient into which the resulting isolated and activated stem cells will later implanted.

Active Agents

Active agents are used in the methods and devices described herein to promote the formation and/or differentiation of stem cells into osteogenic cells. Such active agents can be, for example, small molecules, peptides, growth factors, cytokines, ligands, hormones, and other molecules that regulate growth and differentiation. The active agent(s) can be captured from an autologous source, be obtained from a commercial source, or can be manufactured (e.g., by recombinant procedures).

Examples of active agents that can be employed include TGF, FGF, PDGF, BMP, IGF, interleukins, IL-1, IL-11, TGF, NGF, EGF, HGF, simvastatsin, dexamethasone, oxysterols, sonic hedgehog, interferon, fibronectin, "RGD" or integrin peptides and/or protein, keratinocyte growth factor, osteogenic proteins, MSX1, NFKB1, RUNX2, SMAD1, SMAD2, SMAD3, SMAD4, SOX9, TNF, TWIST1, VDR., AHSG, AMBN, AMELY, BGLAP, ENAM, MINPP1, STATH, TUFT1, BMP1, COL11A1, SOX9, ALPL, AMBN, AMELY, BGLAP, CALCR, CDHI 1, DMP1, DSPP, ENAM, MINPP1, PHEX, RUNX2, STATH, TFIP 11, TUFT1, BGLAP, BMP3, BMP5, BMP6, COL10A1, COL12A1, COL1A1, COL1A2, COL2A1, COMP, FGFR1, GDF10, IGF1, IGF2, MSX1, ANXA5, CALCR, CDH11, COMP, DMP1, EGF, MMP2, MMP8, COL10A1, COL14A1, COL15A1, COL3A1, COL4A3, COL5A1, EGFR, FGF1, FGF3, IGF1R, TGFB2, VEGFA, VEGFB, COL4A3, CSF3, FLT1, IGF1, IGF1R, IGF2, PDGFA, SMAD3, TGFB1, TGFB2, TGFB3, TGFBR2, VEGFA, VEGFB, BMP1, CSF2, CSF3, FGFR1, FGFR2, FLT1, GDF10, IGF1, IGF1R, LGF2, PDGFA, TGFB1, TGFB2, TGFB3, TGFBR1, TGFBR2, VEGFA, VEGFB, AHSG, SERPINH1, CTSK, MMP10, MMP9, PHEX, AMBN, AMELY, ENAM, STATH, TUFT1, BGN, COMP, DSPP, GDF10, CDH11, ICAM1, ITGB1, VCAM1, ITGA1, ITGA2, ITGA3, ITGAM, ITGB1, CD36, COMP, SCARB 1, AMH, GDF2 (BMP9), GDF3 (Vgr-2), GDFS (CDMP-1), GDF6, GDF7, IGFBP3, IL6, INHA (inhibin a), INHBA (inhibin BA), LEFTY1, LTBP1, LTBP2, LTBP4, NODAL, ACVR1 (ALK2), ACVR2A, ACVRLI (ALK1), AMHR2, BMPR1A (ALK3), BMPR1B (ALK6), BMPR2, ITGB5 (integrin B5), ITGB7 (integrin B7), LTBP1, NR0B1, STAT1, TGFB1I1, TGFBR1, (ALK5) TGFBR2, TGFBR3, TGFBRAP1, CDC25A, CDKN1A (p21WAF1/p21CIP1), CDKN2B (pISLNK2B), FOS, GSC (goosecoid), IGFBP3, ITGBS (integrin B5), ITGB7 (integrin B7), JUN, JUNB, MYC, SERPINE 1 (PA1-1), TGFB1I1, TSC22D1 (TGFB114), TG1F1, DLX2, ID1, ID2, JUNB, SOX4, STAT1, BAMB1, BMPER, CDKN2B (pISLNK2B), CER1 (cerberus), CHRD (chordin), CST3, ENG (Evi-1), EVII, FKBPIB, HIPK2, NBL1 (DAN), NOG, PLAU (uPA), RUNX1 (AML1), SMURF1 and other molecules that regulate growth and differentiation, as well as combinations of these factors.

In some embodiments, the active agents include transforming growth factor beta (TGF-β), fibroblast growth factor (FGF, including acid or basic fibroblast growth factor (FBFa or FBFb), and/or fibroblast growth factor-8 (FGF-8)), platelet-derived growth factor (PDGF), bone morphogenic protein (BMP) family (such as BMP-1, BMP-2, BMP-3, BMP-4, BMP-5, BMP-6 and/or BMP-7), members of the insulin growth factor (IGF) family (e.g., insulin like growth factor-I and/or II), interleukin-I (IL-I), IL-11, simvastatsin, dexamethasone, oxysterols, sonic hedgehog, interferon, tumor necrosis factor, nerve growth factor (NGF), fibronectin, "RGD" or integrin sequences, epidermal growth factor (EGF), hepatocyte growth factor (HGF), keratinocyte growth factor, osteogenic proteins (Ops; such as OP-1, OP-2, OP-3), and other molecules that regulate growth and differentiation, as well as combinations of these factors.

Peptide active agents can also be employed that elicit the same activation response as the full protein. For example, an amino acid fragment of a protein or a peptide with a similar action to the TGF-β, FGFb and/or PDGF can be used. Peptide active agents from any of the active agents described herein or known to have utility for activating stem cells can be employed. In other embodiments, a small molecule activator can be employed to activate the stem cells.

In many embodiments, members of TGF-β family are included as active agents in the methods and devices described herein. The TGF-β family encompasses a group of structurally related proteins, which affect a wide range of differentiation processes during embryonic development. Inclusion in the TGF-β family is based on primary amino acid sequence homologies including conservation of seven cysteine residues. The family includes, for example, Mullerian inhibiting substance (MIS), which is required for normal male sex development (Bebringer, et al., Nature, 345:167, 1990), *Drosophila* decapentaplegic (DPP) gene product, which is required for dorsal-ventral axis formation and morphogenesis of the imaginal disks (Padgett, et al., Nature, 325:81-84, 1987), the *Xenopus* Vg-1 gene product, which localizes to the vegetal pole of eggs (Weeks, et al., Cell, 51:861-867, 1987), the activins (Mason, et al., Biochem, Biophys. Res. Commun., 135:957-964, 1986), which can induce the formation of mesoderm and anterior structures in *Xenopus* embryos (Thomsen, at al., Cell, 63:485, 1990), and the bone morphogenetic proteins (BMP's, such as BMP-2 to BMP-5) which can induce de novo cartilage and bone formation (Sampath, et al., J. Biol. Chem., 265: 13198, 1990). The TGF-β gene products can influence a variety of differentiation processes, including adipogenesis, myogenesis, chondrogenesis, hematopoiesis, and epithelial cell differentiation (for a review, see Massague, Cell 49:437, 1987), which is incorporated herein by reference in its entirety.

The proteins of the TGF-β family are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-β's (Cheifetz, et al., Cell, 48:409, 1987), heterodimers have also been detected, and these appear to have different biological properties than the respective homodimers.

Members of the superfamily of TGF-β genes include TGF-β3, TGF-β2, TGF-β4 (chicken), TGF-β1, TGF-5 (*Xenopus*), BMP-2, BMP-4, *Drosophila* DPP, BMP-5, BMP-6, Vgr1, OP-1/BMP-7, *Drosophila* 60A, GDF-1, *Xenopus* Vgf, BMP-3, Inhibin-βA, Inhibin-βB, Inhibin-α, and MIS. These genes are discussed in Massague, Ann. Rev. Biochem. 67:753-791, 1998, which is incorporated herein by reference in its entirety.

In some embodiments, the member of the family of TGF-β employed in the devices and methods described herein is TGF-β3.

Fibroblast Growth Factors and their Receptors Fibroblast growth factors (FGFS) comprise a family of evolutionarily conserved polypeptides involved in a variety of biological processes including morphogenesis, angiogenesis, and tissue remodeling as well as in the pathogenesis of mnerous diseases (reviewed in Ornitz, Bioessays 22: 108, 2000, specifically incorporated by reference herein in its entirety). The various members of this family stimulate the proliferation of a wide spectrum of cells, ranging from mesenchymal to epithelial and neuroectodermal origin in vitro and in vivo. FGFs are expressed in a strict temporal and spatial pattern during development and have important roles in patterning and limb formation (Omitz, Bioessays 22:108, 2000).

All members of the FGF family share a homology core domain of about 120 amino acids, where 28 amino acid residues are highly conserved and six are identical. Structural studies on several FGFs identified 12 antiparallel β strands each one adjacent to β-loops comprising the core region, conserved throughout the family. The core domain comprises the primary FGFR and heparin binding sites. Receptor binding regions are distinct from heparin binding regions (reviewed in Ornitz and Itoh, Gen. Biol. 2, 3005.1, 2001).

In some embodiments, the member of the family of FGF employed in the devices and methods described herein is FGF-2.

Platelet-derived growth factor (PDGF) from human platelets contains two polypeptide sequences—the PDGF-B and PDGF-A polypeptides (Antoniades, H. N. and Hunkapiller, M., Science 220:963-965, 1983). PDGF-B is encoded by a gene localized on chromosome 7 (Betsholtz, C. et al., Nature 320:695-699), and PDGF-A is encoded by the sis oncogene (Doolittle, R. et al., Science 221:275-277, 1983) localized on chromosome 22 (Dalla-Favera, R., Science 218:686-688, 1982). The sis gene encodes the transforming protein of the Simian Sarcoma Virus (SSV), which is closely related to PDGF-2 polypeptide. The human cellular c-sis also encodes the PDGF-A chain (Rao, C. D. et al., Proc. Natl. Acad. Sci. USA 83:2392-2396, 1986). Because the two polypeptide chains of PDGF are coded by two different genes localized in separate chromosomes, human PDGF may consist of a disulfide-linked heterodimer of PDGF-B and PDGF-A, or a mixture of the two homodimers (PDGF-BB homodimer and PDGF-AA homodimer), or a mixture of the heterodimer and the two homodimers.

PDGF may be obtained commercially, or from human tissues or cells, e.g., platelets, by solid phase peptide synthesis, or by recombinant. DNA technology. Mammalian cells in culture infected with the Simian Sarcoma Virus, which contains the gene encoding the PDGF-A chain, can synthesize the PDGF-A polypeptide and to process it into a disulfide-linked homodimer (Robbins et al., Nature 305:

605-608, 1983). In addition, the PDGF-A homodimer reacts with antisera raised against human PDGF and the functional properties of the secreted PDGF-A homodimer are similar to those of platelet-derived PDGF. The recombinant PDGF-B homodimer can be obtained by the introduction of cDNA clones of c-sis/PDGF-B gene into mouse cells using an expression vector. A c-sis/PDGF-B clone used for such expression has been obtained from normal human cultured endothelial cells (Collins, T., et al., Nature 216:748-750, 1985).

While many active agents have utility for activating osteogenic stem cells, data generated by the inventors indicates that in some embodiments TGF-β3, FGF-2 and various forms of PDGF are useful. In other embodiments, the devices and methods for activating stem cells include at least TGF-β3 and FGF-2 as active agents.

In some embodiments, the active agents are capable of increasing the expression of bone morphogenetic protein receptor subunit(s) in the progenitor cells of the stem cell mixture. Treatment with such active agents helps, for example, to potentiate the ability of the progenitor cells to respond to endogenous bone morphogenetic proteins at a site of bone injury or bone surgery. Such treatment with active agents can also drive the stem cells to differentiate down an osteoblast pathway.

Bone morphogenic proteins (BMPs) not only induce bone and cartilage formation but are multifunctional cytokines having a wide range of effects on numerous cell types (Hogan et al., Genes Dev. 10:1580-1594 (1996); Reddi et al., Cytokine Growth Factor Rev. 8:11-20 (1997)). BMPs are members of the TGFβ superfamily. There are approximately 15-20 BMPs genes in man, three BMP receptors, and a number of BMP associated proteins that function as BMP antagonists (Yamashita et al. Bone 19:569-574 (1996)). BMP functions through the Smad signal transduction pathway via three BMP receptors, BMPR-1A, -1B, and II. When a BMP dimer binds the type II receptor it complexes and phosphorylates the type I receptor which activates the Smad pathway.

Exposure of primary ostooblasts to exogenous growth factors can modulate the expression of these receptors. Singhatanadgit et. al. (J. Cell Physiol. 209(3): 912-22 (2006)) tested TGF-beta1, FGF-2, PDGF-AB, and BMP-2 treatment of primary osteoblasts, and some effects of these growth factors onintracellular receptors to the cell surface. Yeh et. al. (J. Cell. Physiol. 190(3): 322-31 (2002); J. Cell Physiol. 191(3): 298-309 (2002)) observed a differential regulation pattern of receptor subunit mRNA in fetal rat calvarial cells after exposure to OP-1. Xu et. al. (Growth Factors 24(4): 268-78 (2006)) tested the effects of TGFbeta3 on BMPR-1B. While the factors involved in the signaling pathway of BMPs bound to their respective receptors are generally understood, the regulation and expression patterns of their receptor subunits has not been fully elucidated. Moreover, researchers have not appreciated that treatment of stem cells (e.g., bone marrow) with growth factors for short periods of time, followed by removal of the growth factors, can stimulate the formation ofosteogenic cells and/or osteogenic precursors.

Activating Stem Cells

As illustrated herein, stem cells can be osteogenically activated by transient exposure to active agents. Such activated stem cells differentiate into osteoprogenitors, osteoblasts and/or osteoblastic phenotypic cells. Moreover, removal of the active agents from the activated stem cells yields a mixture of cells that does not include growth factors and cytokines that may have unintended side effects when transplanted into a subject. Hence, there is no need for several days of stem cell culture in a cocktail of biologically active molecules, which can result in ongoing pain and immobility for a patient waiting for treatment, additional surgery for insertion of an implant after initial repair of a bone injury, contamination of the cultured cells, growth of undesirable cell types in the stem cell population or bone aspirate, as well as the additional time and expense of maintaining the culture and caring for the injured patient.

Instead, stem cells can be activated for implantation and stimulation of bone growth by incubation with the active agent(s) for short time periods. Thus, for example, when a patient is admitted for treatment of a bone injury or condition, autologous or allogenic stem cells (e.g., bone marrow aspirate) can be activated while the patient is undergoing surgery and the activated stem cells can immediately be implanted (along with a bone graft substitute, if desired).

The phrase "activating stem cells" as used herein means that the stem cells are induced to differentiate into osteogenic precursor cells, capable of proliferating and subsequently differentiating into bone-forming cells. Such bone-forming cells include osteoblasts and osteoblastic progenitors. Bone-forming cells can be recognized by their expression ofosteospecific markers such as alkaline phosphatase, osteocalcin, osteopontin and BMP receptors, As indicated herein, activation of stem cells can be for just a short period of time, for example, time periods ranging from 5 minutes to 24 hours. Other optimal time frames for exposing stem cells to active agent range from 10 minutes to 2 hours, or 15 minutes to 1 hour. In some embodiment, the stem cells are contacted with one or more active agents for 5 minutes to 1 hour, or the stem cells are contacted with one or more active agents for 5 minutes to 0.5 hours. As illustrated herein, exposure of bone marrow aspirate to active agents for just one hour leads to upregulation in the expression of alkaline phosphatase and BMP receptor subunit(s).

Thus, one aspect of the invention is a method of making an implant for promoting bone growth in a mammal. The method involves exposing stem cells to one or more active agents for 24 hours or less (e.g., about 5 minutes to 24 hours, or about 10 minutes to 2 hours, or about 15 minutes to 1 hour) to form activated stem cells, separating the activated stem cells from the one or more active agents to form an activated stem cell population that is substantially free of active agents, and mixing the activated stem cell population that is substantially free of active agents with a bone graft substitute to thereby make an implant for promoting bone growth in a mammal.

The stem cells are exposed to concentrations of one or more active agents that are sufficient to activate the stem cells to an osteogenic or osteogenic precursor phenotype. One of skill in the art can readily determine what such concentrations are, for example, by observed what concentrations give rise to increases or upregulation in the expression of alkaline phosphatase and BMP receptor subunit(s). Example, of appropriate concentrations of active agents include use of the active agent(s) at concentration of about 0.01 ng/ml to about 1 μg/ml. In some embodiments, the active agents are used in concentrations of about 0.1 ng/ml to about 500 ng/ml, or about 1 ng/ml to about 100 ng/ml.

As described herein, the stem cells can be from any convenient source. However, stem cells that have osteogenic potential or that can be treated (e.g., differentiated) to generate cells with osteogenic potential are preferred. Sources of stem cells that can be used in the methods, devices and implants described herein include bone marrow, adipose tissue, umbilical cord blood, embryonic yolk sac, placenta, umbilical cord, periosteum, fetal and adolescent skin, and blood. In some embodiments, the stem cells are mesenchymal stem cells or a mixture of cells that include mesenchymal stem cells. The stem cells can be autologous, allogeneic or from xenogeneic sources. The stem cells can be embryonic or from post-natal or adult sources. In some embodiments, the stem cells are an autologous or allogenic bone marrow aspirate.

In general, it is not necessary to separate the stem cells from non-stem cells, or to purify the activated (osteogenic) stem cells from other cell types. However, if one of skill in the art wishes to purify stem cells from non-stem cells, or the activated, osteogenic stem cells from non-activated stem cells and other cell types, the person of skill in the art can do so by any convenient procedure. For example, bone marrow can be centrifuged to separate the components of an aspirate into various fractions based on density, and a fraction rich in mesenchymal stem cells can be obtained. The cells can also be subjected to immunopurification using antibodies that recognize and bind to factors expressed on the cell surface of activated osteogenic stem cells (e.g., BMP receptors).

As indicated herein, the active agents used in the methods and devices described herein for activating the stem cells can be any active agent that can activate the osteogenic potential of stem cells. Examples are recited and illustrated herein.

When the stem cells are activated, they begin to express factors characteristic of osteogenic progenitor cells. For example, as illustrated herein, the levels of alkaline phosphatase, an early marker of osteoblast differentiation, expressed by primary human mesenchymal stem cells, are increased. See, for example, FIG. 1, in which increased alkaline phosphatase expression was observed over time in mesenchymal stem cells treated with TGFβ3 (triangles) or FGF-2 (squares) for just 1 hour compared to untreated control cells, indicating that the treated cells exhibited a more potent differentiation response.

Figure 2:
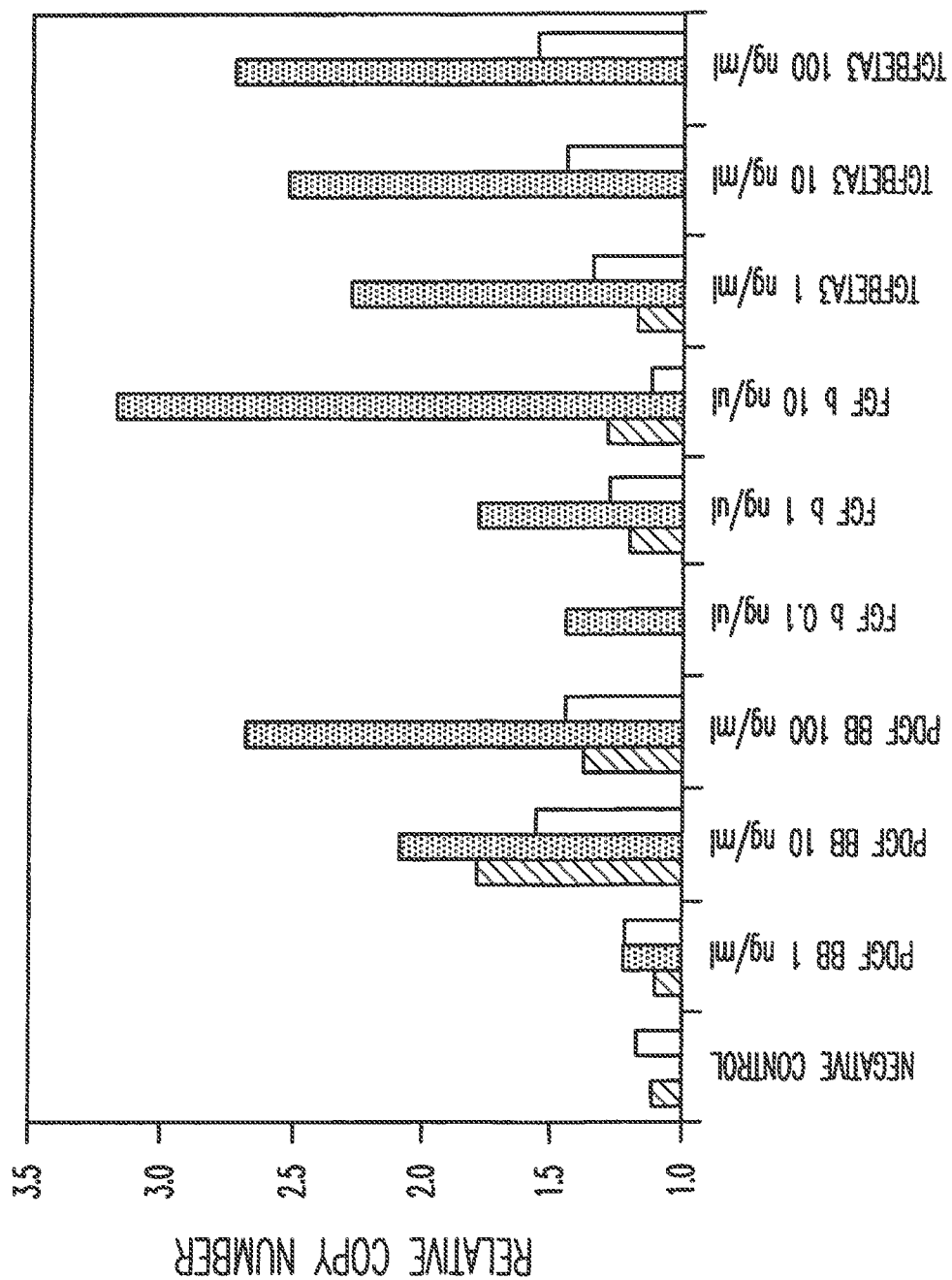
FIG. 2 graphically illustrates relative mRNA copy number for three types of bone morphogenetic protein (hereinafter "BMP") receptor units, namely BMPR-1A ("1A"), BMPR-1B ("1B") and BMPR-II ("II") in primary human mesenchymal cells (hereinafter "MSC's") after the cells were exposed to active agents for 24 hours. The active agents used were platelet-derived growth factor (hereinafter "PDGF BB"), fibroblast growth factor (hereinafter "FGF b"), and transforming growth factor (hereinafter "TGF beta3"), at concentrations of 1 ng/ml, 10 ng/ml and 100 ng/ml, with exposure for 24 hours. Cells were harvested and subjected to a quantitative polymerase chain reaction (hereinafter "PCR"), for all three BMP receptor units, namely -1A, -1B and II as described in Example 1.

In some embodiments, stem cell activation using the methods and devices described herein can also increase the levels of the BMP receptor subunits. As illustrated herein, the mRNA copy number of three BMP receptor units (namely BMPR-1A, BMPR-1B and BMPR-II) in primary mesenchymal stem cells was increased after exposure to active agents (PDGF BB, FGF b and TGF beta3 at 1 ng/ml, 10 ng/ml and 100 ng/ml) for just one (1) hour (FIG. 3) or for 24 hours (FIG. 2). Thus, treatment of stem cells (e.g., mesenchymal stem cells) with active agents for just a short period of time prior to implantation in a surgical site may potentiate the cells for a more robust response after implantation to endogenous BMP.

The activated stem cells are separated from the one or more active agents to which they have been exposed by any convenient method to thereby form an activated stem cell population that is substantially free of active agents. The stem cell population is substantially free of active agents when a composition containing the stem cells (e.g., an implant composition) does not exhibit side effects from the active agent(s) that would preclude administration of the stem cell composition (or implant composition). Thus, small amounts of active agents may remain in the activated stem cell population (or implant composition) so long as the amounts of active agents are, for example, less than 10 ng/ml, or less than 1 ng/ml, or less than 0.1 ng/ml or less than 0.01 ng/ml.

Procedures for separating cells from small and large molecules are available to one of skill in the art. For example, the stem cells can be washed by suspending the cells in media or saline and collecting the cells by centrifugation. Several such washes yield an activated stem cell population that is substantially free of active agents. In another example, the cells can be separated from active agents by passing the cells through a column that retains the active agents but allows the cells to pass through. Such a column can have a matrix that binds or retains the active agent(s); for example, the column can be a gel filtration column, an affinity purification column, or an ion-exchange column.

Thus, the active agent(s) can be introduced to the stem cell source (i.e., bone marrow aspirate) in solution. After a given incubation time, the activated stem cells are separated from the active agents by a procedure that involves filtration, gel filtration, immunoprecipitation, immune-absorption, column chromatography or a combination thereof. For example, the active agents can be removed using an antibody or binding protein or peptide to immobilize the active agents and allow removal or separation of the active agent from the stem cells. In some embodiments, active agents in solution may be removed from the cells via an intraoperative filtration process, such as tangential flow filtration, with the appropriate molecular weight cutoff so as to allow for the intraoperative removal of the active agent from solution.

In another embodiment, the isolated stem cells are incorporated into a bone graft substitute and then exposed to the active agent(s) as described herein. The active agents can be removed from the complex of the stemcells/bone graft substitute by any convenient procedure, for example, by several rounds of sedimentation of the complex of the stemcells/bone graft substitute with removal of a liquid supernatant wash that contains the active agent(s).

In some embodiments, the activated stem cells are separated from the one or more active agents to which they have been exposed by using the device described herein.

Devices for Activating Stem Cells

Another aspect of the invention is a device that activates stem cells, for example, to differentiate into cells that can stimulate bone growth (e.g., osteogenic progenitor cells, osteoblasts and the like). Use of the device in the methods described herein permits incubation of stem cells, stem cell mixtures and stem cell compositions (e.g., implant compositions) with at least one active agent for a time sufficient to activate the stem cells, and then allows separation of the activated stem cells from the at least one active agent, to yield activated stem cells and/or activated stem compositions that are substantially free of active agents.

Thus, for example, one aspect of the invention is a device that includes a solid support and one or more active agents attached to the solid support. The active agent(s) can be directly attached to the solid support (e.g., by adsorption or via a covalent bond) or the active agent(s) can be indirectly attached to the solid support (e.g., via a linker, antibody, peptide, aptamer, alkylene chain, biotin-streptavidin, etc.).

The solid support can be any material to which an active agent can be directly or indirectly attached where the material does not bind or adversely interact with stem cells. Thus, the solid support can be a column matrix material, a filter, an culture plate, tube or dish, a microtiter plate (or the wells of the microtiter plate), a bead (e.g., magnetic beads), a disk, and other materials compatible with stem cells. The solid support can be made from a variety of materials such as plastic, cellulose, cellulose derivatives, magnetic particles, nitrocellulose, glass, fiberglass, latex, and other substrate materials. If desired the solid support can be coated with a substance that inhibits binding of the stem cells or that reduces the reactivity of the materials in the solid support.

The active agent(s) may be attached to the solid support using a variety of techniques known to those of skill in the art, which are amply described in the patent and scientific literature. In the context of the present invention, the term "attached" or "attachment" refers to both noncovalent association, such as adsorption, covalent attachment (which may be via direct linkage between the active agent and functional groups on the support or may be via indirect linkage).

Adsorption onto some solid support materials (e.g., plastic) may be achieved by contacting the active agent, in a suitable buffer, with the solid support for a suitable amount of time. The contact time varies with temperature, but is typically between about 1 hour and about 1 day. In general, for example, contacting a well of a plastic microtiter plate (such as polystyrene or polyvinylchloride) with an amount of active agent ranging from about 10 ng to about 10 µg, and preferably about 100 ng to about 1 µg, is sufficient to immobilize an adequate amount of the active agent.

Covalent attachment of active agent to a solid support may generally be achieved by first reacting the support with a bifunctional reagent that will react with both the support and a functional group, such as a hydroxyl or amino group, on the active agent. For example, the active agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13). The bifunctional reagent can be a cross linking agent, a linker with two functional groups, a peptide, an alkylene chain, an aptamer, or other bifunctional molecules.

The active agent may be non-covalently attached to the solid support via a binding agent such as an antibody where the antibody is attached or adsorbed to the solid support and binds the active agent non-covalently. Alternatively, the active agent may be non-covalently attached to the solid support via biotin-streptavidin, where either the biotin or the streptavidin is attached to the solid support. When the streptavidin is attached to the solid support, biotin is attached to the active agent. The biotin linked to the active agent will bind to the streptavidin, thereby immobilizing the active agent onto the solid support.

In one example, a column matrix or filter material is included, to which the active agent is covalently bound. The stem cells (e.g., bone marrow aspirate) can then be passed through, or incubated in, this substrate for some period of time, for example time frames ranging from 5 minutes to 24 hours with optimal time frames ranging from 15 minutes to 1 hour.

This exposure to the active agent(s) has been shown to increase BMP receptor subunit and alkaline phosphatase expression. For example, FIGS. 2 and 3 illustrate that three active agents (PDGF BB, FGF b, and TGF-β3) upregulate the BMPR-1B subunit, and at specific concentrations, the BMPR-1A and BMPR-II subunits are increased over background. Exposure to such active agents serves to activate or trigger the mesenchymal stem cells to enhance the osteoblast phenotype.

The active agent can therefore be FGF b, TGF-β3 and/or PDGF BB. In other embodiments, the active agents on the solid support can include BMP polypeptides. Other active agents can be attached onto the solid support as well, for example, any of the active agents listed herein. The active agent can be from an autologous source, and allogenic or may be manufactured (e.g. via recombinant technology).

Several or many active agents can be attached onto the same solid support. For example, it is generally accepted that BMPs are more powerful at heterodimers (i.e. BMP-2/BMP-7 combination) than in the homodimeric formulation in which they are currently commercially available. Consequently, for the device and method embodiments described herein the active agents can be attached to a solid support and subsequently separated from the BMA prior to reimplantation. Thus, there is added flexibility as to the possibility of using multiple active agents that can be employed for the current device and in the methods described herein.

In some embodiments, the device is adapted to expose an implant composition to one or more active agents for a selected time (e.g., 24 hours or less, and/or other times described herein) in order to activate stem cells in the implant composition. Such devices are adapted to allow incubation of the implant composition with at least one of the active agents described herein, and then to allow separation of the active agent(s) from the implant composition. Thus, the implant material (e.g., bone graft substitute) and the stem cells within the implant composition can be retained in the device while the active agents are removed. Use of the device yields an implant composition that is substantially free of active agents.

The devise can therefore include a means for separating the stem cells and/or bone graft substitute from the active agent(s). For example, the devise can include a filter that excludes larger materials such as the stem cells and/or the bone graft substitute, but that permits the active agent(s) in solution to pass through the filter material, thereby separating the stem cells and/or bone graft substitute from the active agents. After incubation of the implant composition with the active agent(s), the incubation chamber holding implant composition and the active agent(s) can be drained and rinsed with an appropriate medium (e.g., a buffer, saline, buffered saline, culture medium). Thus, the device can yield a stem cell composition (e.g., an implant composition) that contains activated stem cells and that is substantially free of active agent(s).

The devices described herein can further include a timer for controlling the time for incubating the stem cells with the at least one active agent. For example, the timer can trigger separation of the at least one active agent from the stem cell after the incubating step (i). Thus, for example, the timer can initiate drainage or removal of a solution containing at least one active agent. In addition, or alternatively, the timer can initiate addition of a solution to wash the stem cells and/or bone graft substitute materials. In some embodiments, the device with the timer controls the time for incubating the stem cells with the at least one active agent to 24 hours or less. In other embodiments, the device with the timer controls the time for incubating the stem cells with the at least one active agent to 5 minutes to 1 hour.

Implants

In one embodiment, activated stem cells (e.g., bone marrow aspirate) prepared as described herein are further combined with synthetic bone graft substitutes, such as beta tricalcium phosphate (beta-TCP) to form an implant composition. In one example, a composite of activated stem cells (e.g., activated bone marrow aspirate) and synthetic bone graft substitute is used in place of a tissue graft. Stem cells can be combined with the synthetic bone graft substitute either before or after the stem cells are activated by exposure to the active agent(s). However, prior to implantation, the stem cells are exposed or contacted with active agent(s) so that the stem cells in the implant composition are activated stem cells.

The bone graft substitute can be a solid material which, when placed in, or in juxtaposition to, living bone under suitable conditions, serves as a scaffold for the formation of new bone by bone-forming activated stem cells. Examples of bone graft substitutes that can be employed are described in U.S. Pat. Nos. 5,383,931; 6,461,632; 7,044,972; 7,494,950; and US application publication number 20060008504, which are each specifically incorporated by reference herein in their entireties.

The bone graft substitute can include a calcium salt-containing component. For example, the bone graft substitute can include monocalcium phosphate monohydrate, α-tricalcium phosphate, calcium carbonate, demineralized bone, sodium phosphate salt and, optionally, a polymer. The polymer can be a resorbable polymer. In some embodiments, the polymer includes homopolymer or copolymer fibers having a fiber length of not more than about 15 mm, an aspect ratio from about 50:1 to about 1000:1, or both (and optionally also include continuous reinforcing fibers).

The polymer can be collagen, gelatin, hyaluronic acid, a hyaluronate salt, hydroxypropylcellulose (HPC), carboxymethylcellulose (CMC), hydroxypropyl methylcellulose (HPMC), hydroxyethylcellulose (HEC), xantham gum, guar gum, and/or alginate.

Examples of bone graft substitutes that can be employed include, without limitation, beta-TCP (e.g., chronOS made by Synthes), collagen, bioglass (e.g., 45S5 BioGlass), BioOss (calcium phosphate-based bone graft substitute), Pepgen P-15 (synthetic P-15 peptide bound to a natural form of hydroxylapatite) and AlloGraft (demineralized bone matrix, allograft-based bone graft substitute).

In general, the activated stem cells are incubated or mixed with the bone graft substitute to form an implant composition. In some embodiments, the implant composition is a putty; in other embodiments the implant composition is sufficiently fluid to flow through a syringe needle. For example, the implant composition can have a ratio of liquid components to solid components from about 0.3 to about 0.0 or about 0.41 to about 0.55.

Another embodiment includes use of an active agent in combination with a stem cell source (i.e. BMA), ex vivo, for a short period of time (i.e., 5 min to 60 min) in order to stimulate the stem cells down an osteoblastic pathway. After the ex vivo incubation, the combination of stem cells and active agent are implanted together.

Methods of Treatment

The implant compositions containing the activated stem cells and the bone graft substitute are useful for repairing and treating bone injuries, disorders and conditions. Such bone injuries, disorders or conditions are characterized by bone loss (osteopenia or osteolysis) or by bone damage or injury. Such bone injuries, disorders and conditions include but are not limited to broken bones, bone defects, bone transplant, bone grafts, bone cancer, joint replacements, joint repair, fusion, facet repair, bone degeneration, dental implants and repair, bone defects resulting from disease (e.g., arthritis), bone defects resulting from reconstructive surgeries, and other conditions associated with bone and boney tissue. Examples of bone defects include but are not limited to a gap, deformation or a non-union fracture in a bone. Examples of bone degeneration include but are not limited to osteopenia or osteoporosis. In one embodiment, the bone defect is due to dwarfism. The compositions are also useful for joint replacement or repair wherein the joint is vertebral, knee, hip, tarsal, phalangeal, elbow, ankle, sacroiliac or other articulating/non-articulating joint.

The implant composition can be administered by pressing or incorporating the composition into a bone site, or by injection of the implant composition. When administered by injection, the syringe may have a needle with a gauge of from about 12 to about 18 where the maximum injection pressure employed is not more than about 40 pounds, In one embodiment, the composition also includes continuous reinforcing fibers.

The following nonlimiting Examples further illustrate certain aspects of the invention.

Example 1

Materials and Methods

The following materials and methods were used to develop certain aspects of the invention.

Differentiation of Cells

Human mesenchymal stem cells (Lonza, Walkersville, Md.) at passage 3 were seeded in basal medium (Stem Cell Technologies, Vancouver, Canada) at a density of $6 \times 10^4$ cells/35 mm well and incubated for 2 days at 37° C. Cells were rinsed with PBS, activated with 100 ng/ml of growth factor (FGF-2 or TGFβ3, R&D Systems, Minneapolis, Minn.) in fresh basal medium for 1 hour, rinsed with PBS and then incubated in either fresh basal medium or osteogenic differentiation medium (Stem Cell Technologies, Vancouver, Canada) for 7-14 days at 37° C.

Real Time PCR

Total RNA was prepared from cells treated with various active agents using RNeasy Plus Mini Kit and QIA shredder Mini Spin columns (Qiagen). Total RNA was also prepared from untreated cells as a control cDNA was generated using random hexamer and Oligo dT following the TaqMan Reverse Transcription Kit (Applied Biosystems). Primer and probe sets for real-time were as follows:

```
huBMPR1A_2 fwd (SEQ ID NO: 1):
5'-TAACCAGTATTTGCAACCCAC ACT-3'.

huBMPR1A_2 rev (SEQ ID NO: 2):
5'-GAGCAAAACCAGCCATCGAA-3'.

huBMPR1A_2 Probe (SEQ ID NO: 3):
5'-CCC CCT GTT GTC ATA GGT CCG TTT TTT GAT-3'
(FAM/TAMRA).

huBMPR1B_1 fwd (SEQ ID NO: 4):
5'-CCA AAG GTC TTG CGT TGT AAA TG-3'.

huBMPR1B_1 rev (SEQ ID NO: 5):
5'-CAT CGT GAA ACAATA TCC GTC TGT-3'.

huBMPR1B_1 Probe (SEQ ID NO: 6):
5'-CCA CCA TTG TCC AGA AGA CTC AGT CAA CAA-3'
(FAM/TAMRA)

huBMPR2_2 fwd (SEQ ID NO: 7):
5'-TGC CCT GGC TAC CAT GGA-3' huBMPR2_2 rev (SEQ ID NO: 8):
5'-CGC ACA TAG CCGTTCTTGATT-3' huBMPR2_2 Probe (SEQ ID NO: 9):
5'-TCA GCA CTG CGG CTG CTT CGC-3'
(FAM/TAMRA)
```

Samples were run on an Applied Biosystems 7500 Fast Real-Time PCR System as a multiplex reactions with beta 2 mieroglobulin endogenous controls (VIC/TAMRA) (Applied Biosystems).

Alkaline Phosphatase Assay

Human mesenchymal stem cells (Lonza, Walkersville, Md.) at passage 3 were seeded in basal medium (Stem Cell Technologies, Vancouver, Canada) at a density of $6 \times 10^4$ cells/35 mm well and incubated for 2 days at 37° C. Cells were rinsed with PBS, activated with 100 ng/ml of growth factor (FGF-2 or TGFβ3, R&D Systems, Minneapolis, Minn.) in fresh basal medium for 1 hour, rinsed with PBS then incubated in either fresh basal medium or osteogenic differentiation medium (Stem Cell Technologies, Vancouver, Canada) for 7-14 days at 37° C. At the time of assay, cells were rinsed twice with PBS, harvested in 100 μl/35 mm well lysis buffer and frozen/thawed twice in liquid nitrogen. Alkaline phosphatase activity was determined by incubation of 20 μl lysate with 20 μl 1 mg/ml p-nitrophenyl phosphate for 3 minutes and measurement of the resulting luminescence at 405 nm. Alkaline phosphatase activity was normalized according to cell content, as determined by CyQuant (Invitrogen, Carlsbad, Calif.) DNA quantification.

Immobilization

For initial studies, active agents (e.g. growth factors) were immobilized onto microtiter wells as follows.

Biotinylated anti-growth factor antibody (500 ng) (R&D Systems, Minneapolis, Minn.) was incubated in 200 μl PBS/well of a streptavidin-coated 96-well plate for 30 minutes, rinsed 3 times with PBS and then bound to increasing quantities of growth factor in 200 μl PBS for 30 minutes. After 3 rinses with PBS, the presence of the growth factor was detected by incubation with 1 μg of a second, unlabeled anti-growth factor antibody in 200 μl PBS with 0.1% BSA for 30 minutes. The wells were washed three times with PBS, incubated with 1 μg of horseradish peroxidase-conjugated secondary antibody in 200 μl PBS with 0.1% BSA for 30 minutes, and rinsed again with PBS three times. The immobilized antibody-growth factor-secondary antibody was then incubated with 200 μl enhanced chemiluminescent substrate for 1 minute. Quantification of the amount of immobilized horseradish peroxidase-conjugated secondary antibody was performed by measurement of chemiluminescent emission at visible wavelengths.

Activity Assays

To determine the bioactivity of tethered active agents prior to the stem cell activation step, the following assays were formed. For studies involving FGF-2, Swiss Albino 3T3 cells (ATCC, Manassas, Va.) were seeded in 10% serum basal medium at a density of $4 \times 10^5$/35 mm well, incubated for 1 day at 37° C., rinsed 3 times with PBS and then synchronized in 0.5% serum basal medium for 1 day at 37° C. FGF2 (R&D Systems, Minneapolis, Minn.) and a 50 fold excess of biotinylated anti-FGF2 antibody (R&D Systems, Minneapolis, Minn.) were complexed in 0.5% serum basal medium for 15 minutes. The synchronized cells were rinsed 3 times with PBS then treated with the FGF2/biotinylated anti-FGF2 antibody complex for 30 minutes at 37° C. At the endpoint of the assay, cells were rinsed 3 times with PBS, harvested in SDS sample buffer and heated for 10 minutes at 90° C. The resulting lysates were fractionated by SDS-PAGE, transferred to a PVDF membrane and sequentially probed with a 1:10000 dilution of anti-phospho-ERK (Cell Signaling Technology, Beverly, Mass.) antibody, followed by a 1:10000 dilution of a horseradish peroxidase-conjugated secondary antibody (Santa Cruz Biotechnology, Santa Cruz, Calif.). Horseradish peroxidase activity was determined by exposure to enhanced chemiluminescent substrate for 1 minute, visualized by CCD camera and densitometrically quantified using ImageJ analysis program.

For the TGFβ3 activity assay, Mv1Lu mink lung cells (ATCC, Manassas, Va.) were seeded in basal medium at a density of $4 \times 10^3$ cells/well of a 96-well plate and incubated for 1 day at 37° C. TGFβ3 (R&D Systems, Minneapolis, Minn.) and a 50 fold excess of biotinylated anti-TGFβ3 antibody (R&D Systems, Minneapolis, Minn.) were complexed in basal medium for 15 minutes. After 3 rinses with PBS, cells were treated with the TGFB3/biotinylated anti-TGFβ3 antibody complex for 3 days at 37° C. At the time of assay, TGFβ3 treatment medium was supplemented with CellTiter-Glo ATP detection reagent (Promega, Madison, Wis.), incubated 5 minutes and cell number was quantified by measurement of chemiluminescent emission at visible wavelengths.

Example 2

Results

Primary human mesenchymal stem cells are capable of differentiating down an osteoblastic lineage. This is demonstrated in vitro by culturing cells in an osteogenic cocktail containing, but not limited to, dexamethasone, ascorbic acid and β-glycerophosphate. Under these culture conditions cells show an upregulation of osteoblast differentiation markers, the most common of which is the early marker alkaline phosphatase.

FIG. 1 shows a slight upregulation in alkaline phosphatase activity in the untreated mesenchymal stem cells (circles) from days 10 to 12, as expected. However, when the mesenchymal stem cells were pretreated with TGFβ3 (triangles) or FGF-2 (squares) for 1 hour, followed by removal of the agents and culture in differentiation media, the level of alkaline phosphatase activity increased significantly 2-3 fold.

These data indicate that just a 1 hour treatment of mesenchymal stem cells with either TGFβ3 or FGF-2 on day 0 can impact osteoblast differentiation such that the markers of osteoblast formation are upregulated 10+ days post treatment.

Mesenchymal stem cells respond to bone morphogenetic proteins both in vitro and in vivo to induce an osteoblast phenotype. BMPs act via a receptor complex made up of three subunits, BMPR-1A, BMPR-1B, and BMPR-II. When MSCs were treated with selected active agents (PDGF-BB, TGFbeta3, and FGF-2) for 24 hours, the relative copy number of the BMPR-1B gene increased significantly over untreated cells. However, FIG. 3 shows that a similar response was observed after just 1 hour of treatment.

These data indicate that an intraoperative time frame of just 1 hour is sufficient to treat MSCs with an active agent such that the level of receptors for the BMP ligand can be increased over untreated cells. The presence of increased levels of BMP receptors on mesenchymal stem cells potentiates these cells for a BMP-2 osteogenic response in vivo and results in more robust bone healing.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for preparing an implant composition for promoting bone growth in a mammal, comprising:
   (a) contacting stem cells with transforming growth factor beta (TGF-β), fibroblast growth factor (FGF), platelet-derived growth factor (PDGF), or a combination thereof for 5 minutes to 24 hours, wherein the TGF-β, FGF, PDGF, or combination thereof osteogenically activates the stem cells thereby forming a population of osteogenic precursor cells having an activated osteogenic potential,
   (b) separating the TGF-β, FGF, PDGF, or combination thereof from the osteogenic precursor cells to form a population of osteogenic precursor cells that is substantially free of the TGF-β, FGF, PDGF, or combination thereof, and
   (c) mixing the population of osteogenic precursor cells from step (b) with a bone graft substitute to thereby prepare an implant composition for promoting bone growth in a mammal.

2. The method of claim 1, wherein the stem cells are contacted with the TGF-β, FGF, PDGF, or combination thereof for 5 minutes to 1 hour.

3. The method of claim 1, wherein the stem cells are contacted with the TGF-β, FGF, PDGF, or combination thereof for 5 minutes to 0.5 hours.

4. The method of claim 1, wherein the stem cells are from bone marrow, adipose tissue, muscle tissue, umbilical cord blood, embryonic yolk sac, placenta, umbilical cord, periosteum, fetal skin, adolescent skin, or blood.

5. The method of claim 1, wherein the stem cells are autologous, allogeneic, or xenogeneic.

6. The method of claim 1, wherein the stem cells are embryonic, post-natal, or adult stem cells.

7. The method of claim 1, wherein the stem cells comprise mesenchymal stem cells.

8. The method of claim 1, wherein the stem cells comprise autologous bone marrow aspirate.

9. The method of claim 1, wherein the method is performed intraoperatively.

10. The method of claim 8, further comprising, prior to step (a), isolating, concentrating, or isolating and concentrating the stem cells.

11. The method of claim 1, wherein the stem cells are contacted with TGF-β.

12. The method of claim 1, wherein the stem cells are contacted with TGF-beta3, PDGF-AB, PDGF-BB, FGF-2, TGF-beta1, FGF-8, or combinations thereof.

13. The method of claim 1, wherein the stem cells are contacted with FGF.

14. The method of claim 1, wherein the stem cells are contacted with PDGF.

15. The method of claim 1, wherein the TGF-β, FGF, PDGF, or combination thereof are provided in a solution.

16. The method of claim 15, wherein the osteogenic precursor cells are separated from the TGF-β, FGF, PDGF, or combination thereof by a procedure comprising filtration, gel filtration, tangential flow filtration, immunoprecipitation, immuno-absorption, affinity purification column, column chromatography, or a combination thereof.

17. The method of claim 1, wherein the TGF-β, FGF, PDGF, or combination thereof are attached to a solid support.

18. The method of claim 17, wherein at least some of the TGF-β, FGF, PDGF, or combination thereof are attached to a solid support via a peptide, an antibody, a chemical cross linker, or a combination thereof.

19. The method of claim 1, wherein the bone graft substitute comprises a calcium salt.

20. The method of claim 19, wherein the calcium salt comprises monocalcium phosphate monohydrate, α-tricalcium phosphate, β-tricalcium phosphate, calcium carbonate, or a combination thereof.

21. The method of claim 19, wherein the bone graft substitute further comprises demineralized bone, a sodium phosphate salt, a polymer, or a combination thereof.

22. The method of claim 21, wherein the polymer is collagen, gelatin, hyaluronic acid, a hyaluronate salt, hydroxypropylcellulose (HPC), carboxymethylcellulose (CMC), hydroxypropyl methylcellulose (HPMC), hydroxyethylcellulose (HEC), xantham gum, guar gum, alginate, or a combination thereof.

23. The method of claim 1, further comprising implanting the implant composition into a patient.

24. The method of claim 1, wherein steps (a) and (b) are performed using a device, wherein the device comprises a solid support to which the TGF-β, FGF, PDGF, or combination thereof are bound, and wherein step (a) is performed by incubating the device with the stem cells and step (b) is performed by separating the device from the osteogenic precursor cells.

25. The method of claim 24, wherein the TGF-β, FGF, PDGF, or combination thereof are directly bound to the solid support or indirectly bound to the solid support through streptavidin, biotin, a crosslinker, an antibody, or peptide.

26. The method of claim 25, wherein the antibody is an anti-TGF-β antibody, anti-FGF antibody, anti-PDGF antibody, or combination thereof.

* * * * *

SEQUENCE LISTING

<160> NUMBER OF SEQ ID NOS: 9

<210> SEQ ID NO 1
<211> LENGTH: 24
<212> TYPE: DNA
<213> ORGANISM: Homo sapiens

<400> SEQUENCE: 1
taaccagtat ttgcaaccca cact        24

<210> SEQ ID NO 2
<211> LENGTH: 20
<212> TYPE: DNA
<213> ORGANISM: Homo sapiens

<400> SEQUENCE: 2
gagcaaaacc agccatcgaa        20

<210> SEQ ID NO 3
<211> LENGTH: 30
<212> TYPE: DNA
<213> ORGANISM: Homo sapiens

<400> SEQUENCE: 3
ccccctgttg tcataggtcc gttttttgat        30

<210> SEQ ID NO 4
<211> LENGTH: 23
<212> TYPE: DNA
<213> ORGANISM: Homo sapiens

<400> SEQUENCE: 4
ccaaaggtct tgcgttgtaa atg        23

```
<210> SEQ ID NO 5
<211> LENGTH: 24
<212> TYPE: DNA
<213> ORGANISM: Homo sapiens

<400> SEQUENCE: 5
catcgtgaaa caatatccgt ctgt                                          24

<210> SEQ ID NO 6
<211> LENGTH: 30
<212> TYPE: DNA
<213> ORGANISM: Homo sapiens

<400> SEQUENCE: 6
ccaccattgt ccagaagact cagtcaacaa                                    30

<210> SEQ ID NO 7
<211> LENGTH: 18
<212> TYPE: DNA
<213> ORGANISM: Homo sapiens

<400> SEQUENCE: 7
tgccctggct accatgga                                                 18

<210> SEQ ID NO 8
<211> LENGTH: 21
<212> TYPE: DNA
<213> ORGANISM: Homo sapiens

<400> SEQUENCE: 8
cgcacatagc cgttcttgat t                                             21

<210> SEQ ID NO 9
<211> LENGTH: 21
<212> TYPE: DNA
<213> ORGANISM: Homo sapiens

<400> SEQUENCE: 9
tcagcactgc ggctgcttcg c                                             21
```